United States Patent
Lai et al.

(10) Patent No.: US 7,952,822 B2
(45) Date of Patent: May 31, 2011

(54) LENS ACTIVATING DEVICE

(75) Inventors: Mei-Ling Lai, Taiping (TW); Li-Te Kuo, Hsinchu County (TW)

(73) Assignee: Wah Hong Industrial Corp., Kaohsiung (TW)

( * ) Notice: Subject to any disclaimer, the term of this patent is extended or adjusted under 35 U.S.C. 154(b) by 0 days.

(21) Appl. No.: 12/555,739

(22) Filed: Sep. 8, 2009

(65) Prior Publication Data

US 2010/0172041 A1 Jul. 8, 2010

(30) Foreign Application Priority Data

Jan. 7, 2009 (TW) ................................ 98200157 U

(51) Int. Cl.
*G02B 7/02* (2006.01)
(52) U.S. Cl. ..................... 359/824; 359/819; 359/822
(58) Field of Classification Search ............... 359/824
See application file for complete search history.

(56) References Cited

U.S. PATENT DOCUMENTS

| 7,417,811 | B2 * | 8/2008 | Chang | 359/824 |
| 7,697,216 | B2 * | 4/2010 | Wada et al. | 359/694 |
| 2008/0117536 | A1 * | 5/2008 | Higuchi | 359/824 |
| 2008/0247063 | A1 * | 10/2008 | Otsuki et al. | 359/824 |
| 2008/0259467 | A1 * | 10/2008 | Chung | 359/814 |
| 2009/0225452 | A1 * | 9/2009 | Wu | 359/824 |
| 2009/0290241 | A1 * | 11/2009 | Huang et al. | 359/824 |

FOREIGN PATENT DOCUMENTS

| JP | 2003-295033 | 10/2003 |
| JP | 2006-201525 | 8/2006 |
| JP | 2008-026619 | 2/2008 |

* cited by examiner

*Primary Examiner* — Jessica T Stultz
(74) *Attorney, Agent, or Firm* — Pai Patent & Trademark Law Firm; Chao-Chang David Pai

(57) ABSTRACT

A lens activating device includes at least one elastic piece, at least one stationary piece and a movable piece. At least one elastic piece has at least four sheet portions and four sets of elastic portions. Each set of the elastic portions are serpentine and connected between two sheet portions in order to make the at least one elastic piece form a closed ring. The stationary piece is connected to two sheet portions, and the movable portion is connected to the other two sheet portions. The elastic force generated by the four sets of elastic portions exerts a restoring force on the movable piece. Via this arrangement, the slight rotation of the movable piece within the lens activating device can be reduced. Further, the problem that the elastic piece may scrape the neighboring elements can be prevented.

10 Claims, 7 Drawing Sheets

LENS ACTIVATING DEVICE

BACKGROUND OF THE INVENTION

1. Field of the Invention

The present invention relates to a lens activating device, and in particular, to a lens activating device for driving lens of a micro imaging module.

2. Description of Related Art

Recently, it becomes more and more popular for portable devices such as mobile phones or PDA to be equipped with an imaging module. Furthermore, since the market requires these portable devices to have more powerful functions and smaller sizes, it is necessary for the imaging module to generate high quality pictures and to be of small size accordingly. One improvement of picture quality is to increase the number of pixel. The pixel number of an imaging module has already increased from the VGA-level 30 pixels to 2, 3 or even 8 million pixels, which is now common in the market. Another improvement lies in the definition of the image. Thus, the imaging module of a portable device also develops from a fixed-focus mode to auto-focus mode or even optical zoom mode.

The auto-focus mode employs the principle of moving the lens in the imaging module suitably according to various distances of targets, whereby the optical image of the desired target can be focused correctly on an image sensor so as to generate a clear image. The common ways of activating the lens to move in the imaging module include activating by a step motor, piezoelectric motor and voice coil motor (VCM)

In general, the voice coil motor is constituted by disposing a coil in the magnetic circuit of permanent magnets. According to Fleming's left hand rule, when an electric current passes through the coil, a pushing force may be induced by the permanent magnets, thereby moving a supporting base connected to the permanent magnets and thus driving the lens assembly fixed in the supporting base. With the adjustment of current passing through the coil, the optical zoom mode and the auto-focus mode can be achieved.

Please refer to FIG. 1. JP 2006-201525 discloses an elastic piece 1a of a lens driving device, which includes an outer ring 11a, three supporting arms 12a extending and bending continuously from the inner wall of the outer ring 11a, and an inner ring 13a provided in the outer ring 11a and connected to the distal end of the supporting arm 12a. With the inner ring 13a of the elastic piece 1a being fixed to the lens assembly of the lens driving device and the outer ring 11a being fixed to the supporting base, the elastic force of the elastic piece 1a can allow the voice coil motor to be positioned and restored.

Please refer to FIG. 2. JP 2003-295033 discloses an elastic piece 1b of a lens driving device, which includes two curved arms 11b that are symmetric with each other and are formed into C shape and a connecting piece 12b. After the elastic piece 1b is pressed, the curved arm 11b is bent at a first positioning end 111b and then bent reversely to form an elastic arm 112b. The distal end of the elastic piece is formed with a second positioning end 113b. The connecting piece 12b is connected with the two curved arms 11b for positioning these two elastic arms. In mounting, the first positioning end 111b and the second positioning end 113b of the two curved arms 11b are positioned on the lens assembly and the supporting base respectively. After cutting off the connecting piece 12b, the two curved arms 11b can allow the voice coil motor to be positioned and restored.

However, in the above two patent documents, the elastic piece is driven by the lens assembly to move vertically (axially). Thus, the lens assembly may rotate slightly to hit the elastic piece. As a result, the elastic piece may suffer damage and even get failure.

Furthermore, the elastic piece is formed by a pressing process. If the construction of the elastic piece is more complicated, such as that in JP 2006-201525, in which the supporting arm is formed with continuous bends, it is more difficult to develop the press-forming molds for the supporting arm. As a result, the production cost may be inevitably increased and the yield of products may be deteriorated.

According to the JP 2003-295033, after feeding and press-forming the elastic piece, a further cutting process is needed (i.e. cutting off the connecting piece). Thus, the production cost and working hours are increased undesirably.

Please refer to FIGS. 3 and 4 again. JP 2008-026619 also discloses a lens driving device, in which an upper elastic piece 91a is sandwiched between an outer casing 93a and a top frame 94a. An outer ring 912a of the upper elastic piece 91a is fixed between a casing 93a and the top frame 94a. The inner ring 912a of the upper elastic piece 91a is fixed to a lens base 96a, thereby positioning and restoring the lens base 96a. A lower elastic piece 92a is sandwiched between a bottom frame 95a and the lens base 96a. With an insulating ring 97a being disposed around the lens base 96a to press the outer ring 921a of the lower elastic piece 92a, the lower elastic piece 92a can be fixed to the bottom frame 95a. In this way, the outer ring 921a and the inner ring 922a of the lower elastic piece 92a can be secured without flexing.

In addition, it is more important to appreciate that a wrist 913a of the upper elastic piece 91a is connected to the inner ring 911a and the outer ring 912a, and it is used as a flexible section when the outer ring 911a moves with respect to the inner ring 912a. However, such a wrist 913a is formed with continuous bends, so that it cannot be manufactured easily and may suffer damage.

Therefore, in view of the above-mentioned drawbacks, the present Inventor proposes a reasonable and novel structure based on his expert experience and delicate researches so as to solve the drawbacks in prior art.

SUMMARY OF THE INVENTION

The objective of the present invention is to provide a lens activating device, whereby the slight rotation of a movable piece of the lens activating device can be reduced. Further, the problem that the elastic piece may scrape neighboring elements can be prevented.

Another objective of the present invention is to provide a lens activating device, in which the elastic piece is integrally formed so as to simplify the whole structure. Via this arrangement, the difficulty in designing the press-forming mold is reduced. As a result, the production cost is reduced and the yield of products can be improved.

To achieve the above-mentioned objective, the present invention provides a lens activating device, which includes at least one elastic piece, at least one stationary piece and a movable piece. At least one elastic piece has at least four sheet portions and four sets of elastic portions. Each set of the elastic portions are serpentine and connected between two sheet portions in order to make the at least one elastic piece form a closed ring. The stationary piece is connected to two sheet portions, and the movable portion is connected to the other two sheet portions. The elastic force generated by the four sets of elastic portions exerts a restoring force on the movable piece.

To achieve the above-mentioned objective, the present invention provides a lens activating device, which includes at least one first elastic piece, at least one second elastic piece, a stationary piece and a movable piece. At least one first elastic piece has at least four sheet portions and four sets of elastic portions. Each set of the elastic portions are serpentine and connected between two sheet portions in order to make the at least one first elastic piece form a closed ring. At least one second elastic piece has at least four sheet portions and four sets of elastic portions. Each set of the elastic portions are serpentine and connected between two sheet portions in order to make the at least one second elastic piece form a closed ring. The stationary piece is connected to two sheet portions of the first elastic piece and two sheet portions of the second elastic piece. The movable portion is connected to the other two sheet portions of the first elastic piece and the other two sheet portions of the second elastic piece. The elastic force generated by the four sets of elastic portions of the first elastic piece and the four sets of elastic portions exerts a restoring force on the movable piece.

The present invention has advantageous features as follows. By using the elastic piece of a closed ring structure, the slight rotation of the movable piece in the lens activating device can be reduced. Further, the problem that the elastic piece may scrape the neighboring elements can be prevented.

In order to further understand the characteristics and technical contents of the present invention, a description relating thereto will be made with reference to the accompanying drawings. However, the drawings are illustrative only but not used to limit the present invention.

DETAILED DESCRIPTION OF THE PREFERRED EMBODIMENTS

Figure 1:
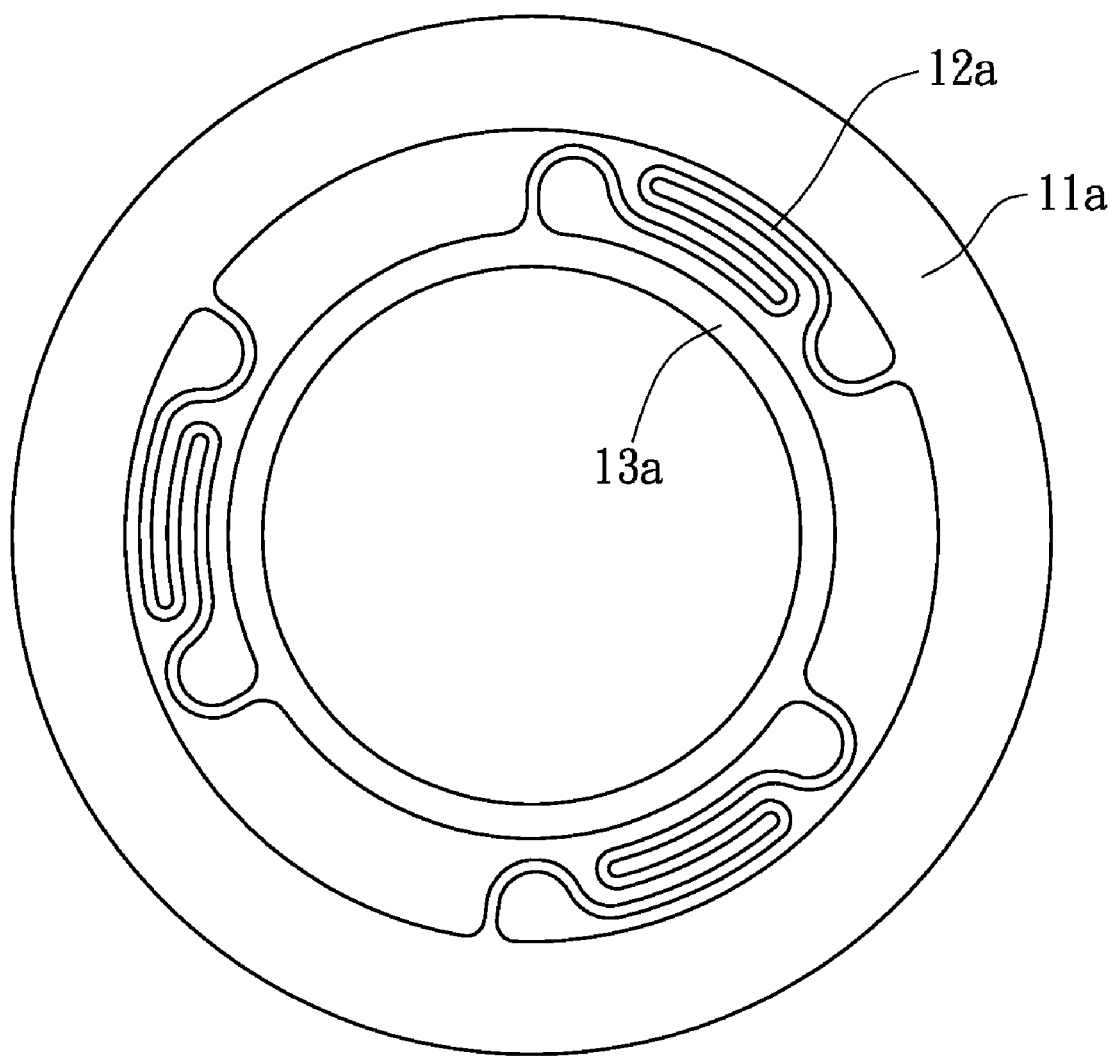
FIG. 1 is a plane view showing the elastic piece of a conventional lens driving device.
Figure 2:
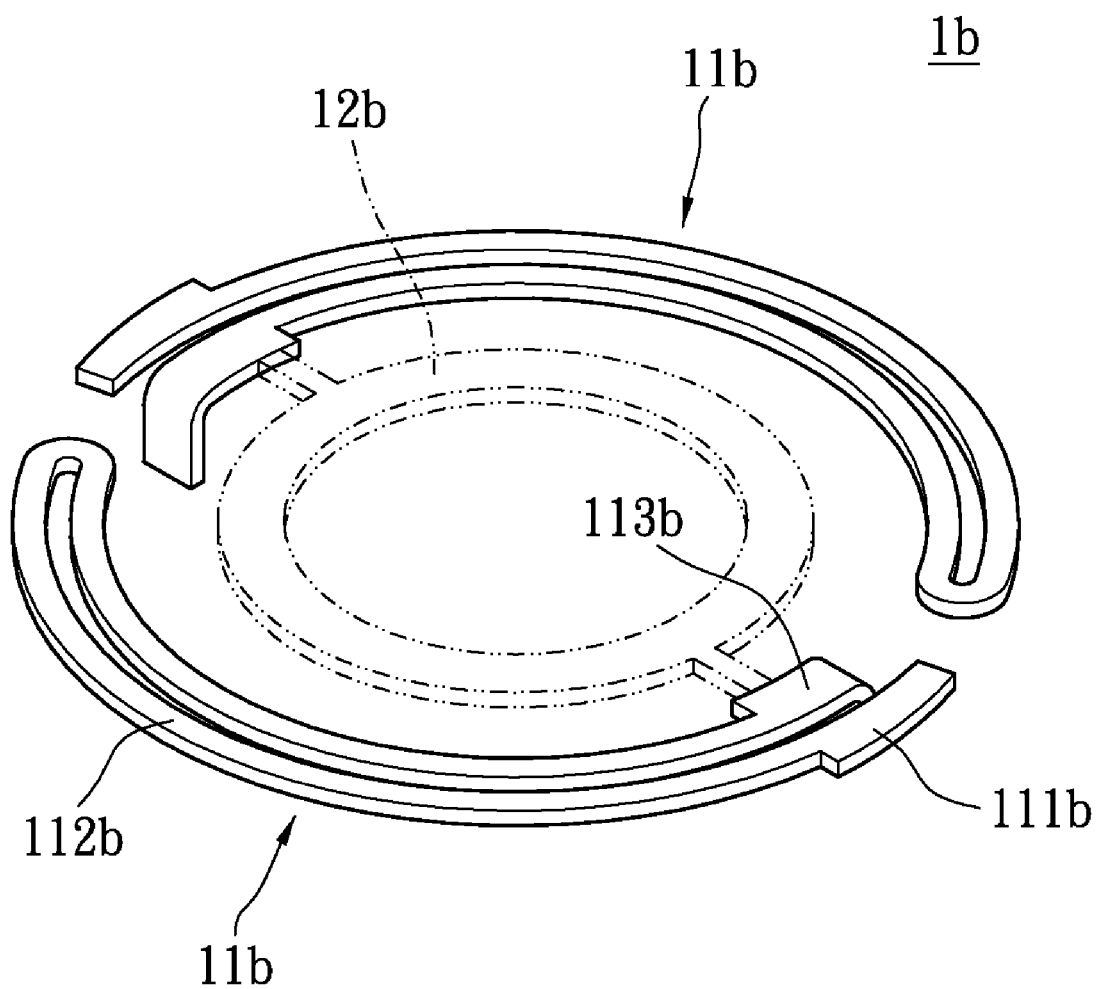
FIG. 2 is a perspective view showing the elastic piece of another conventional lens driving device.
Figure 3:
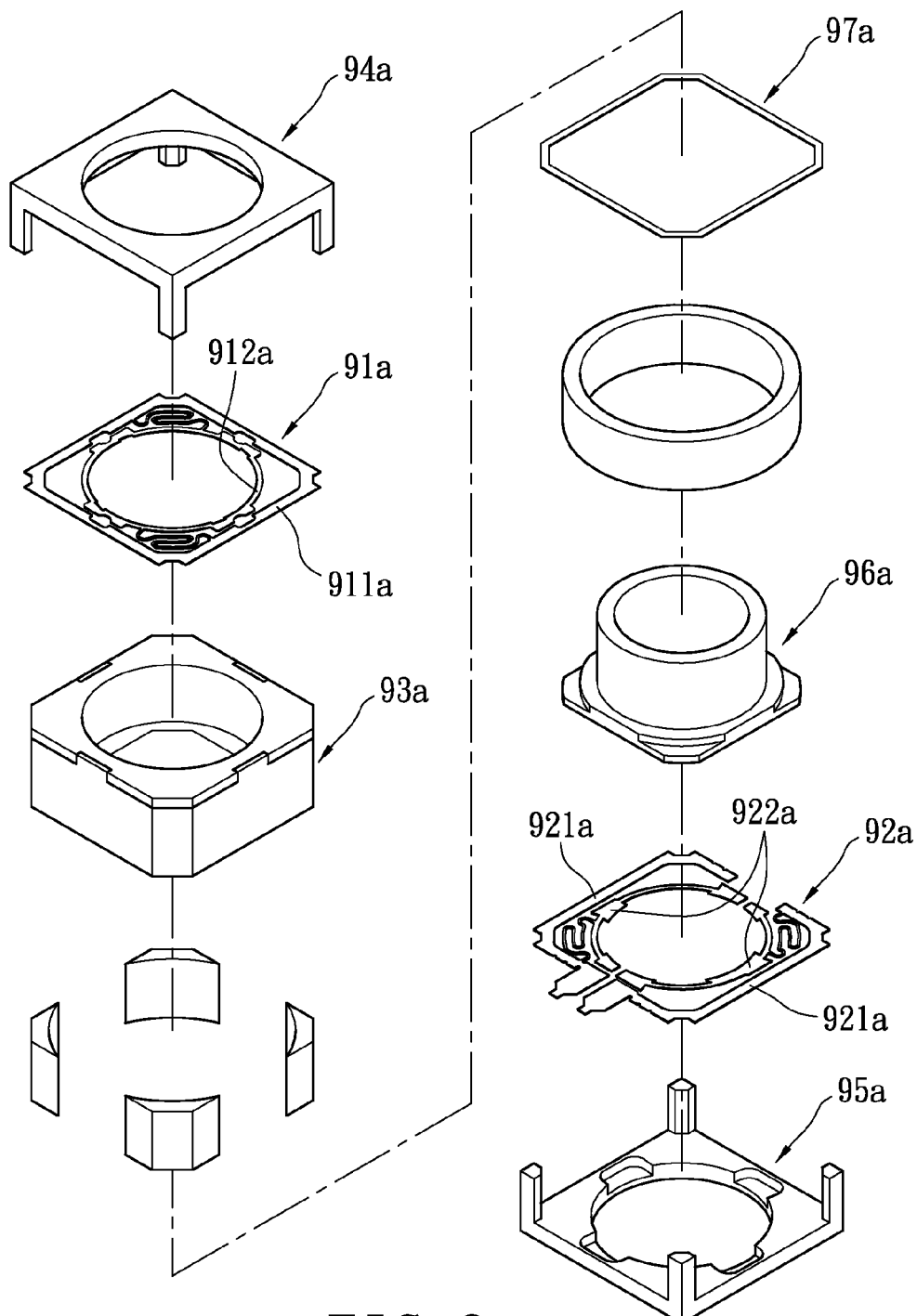
FIG. 3 is an exploded perspective view showing the elastic piece of a further conventional lens driving device.
Figure 4:
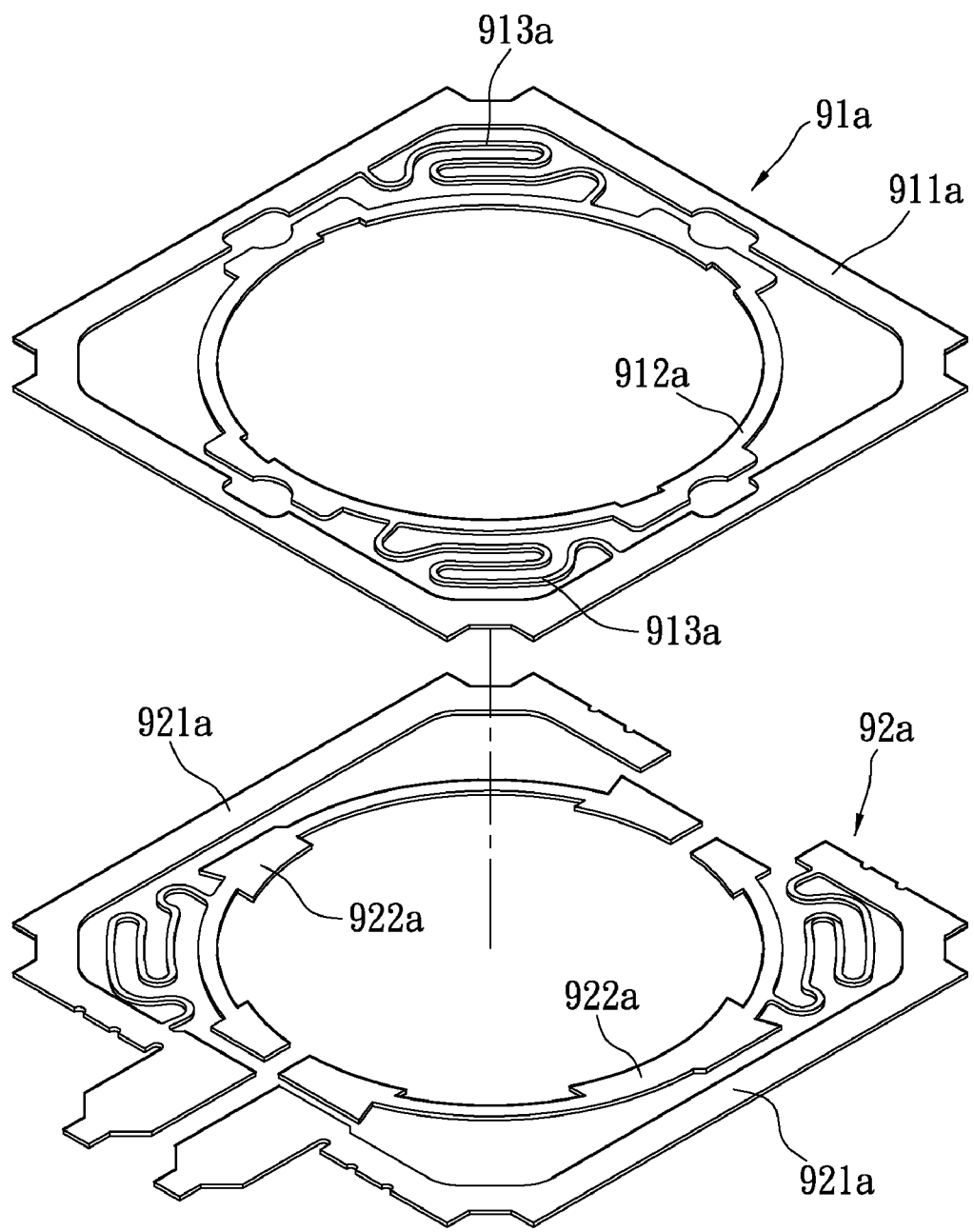
FIG. 4 is a perspective view showing the elastic piece of still a further conventional lens driving device.
Figure 5:
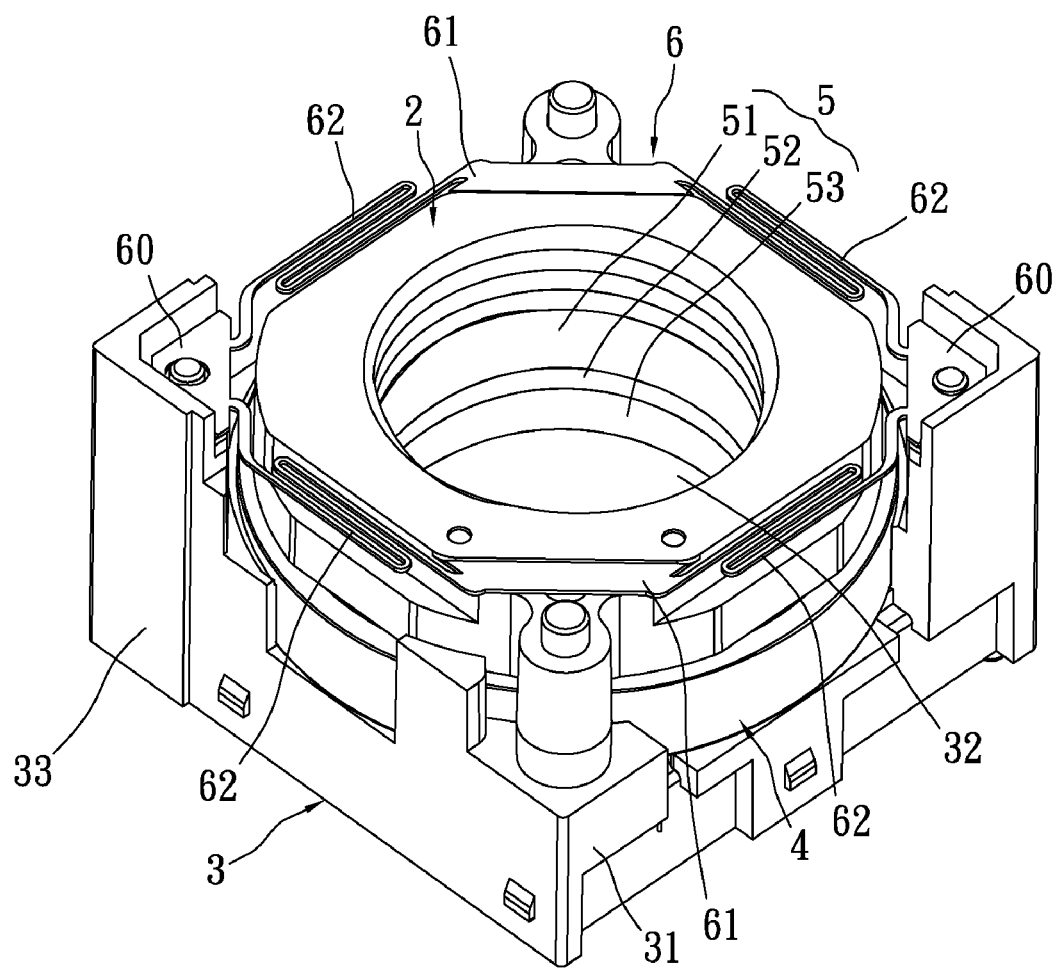
FIG. 5 is an assembled perspective view showing the lens activating device of the present invention.
Figure 6:
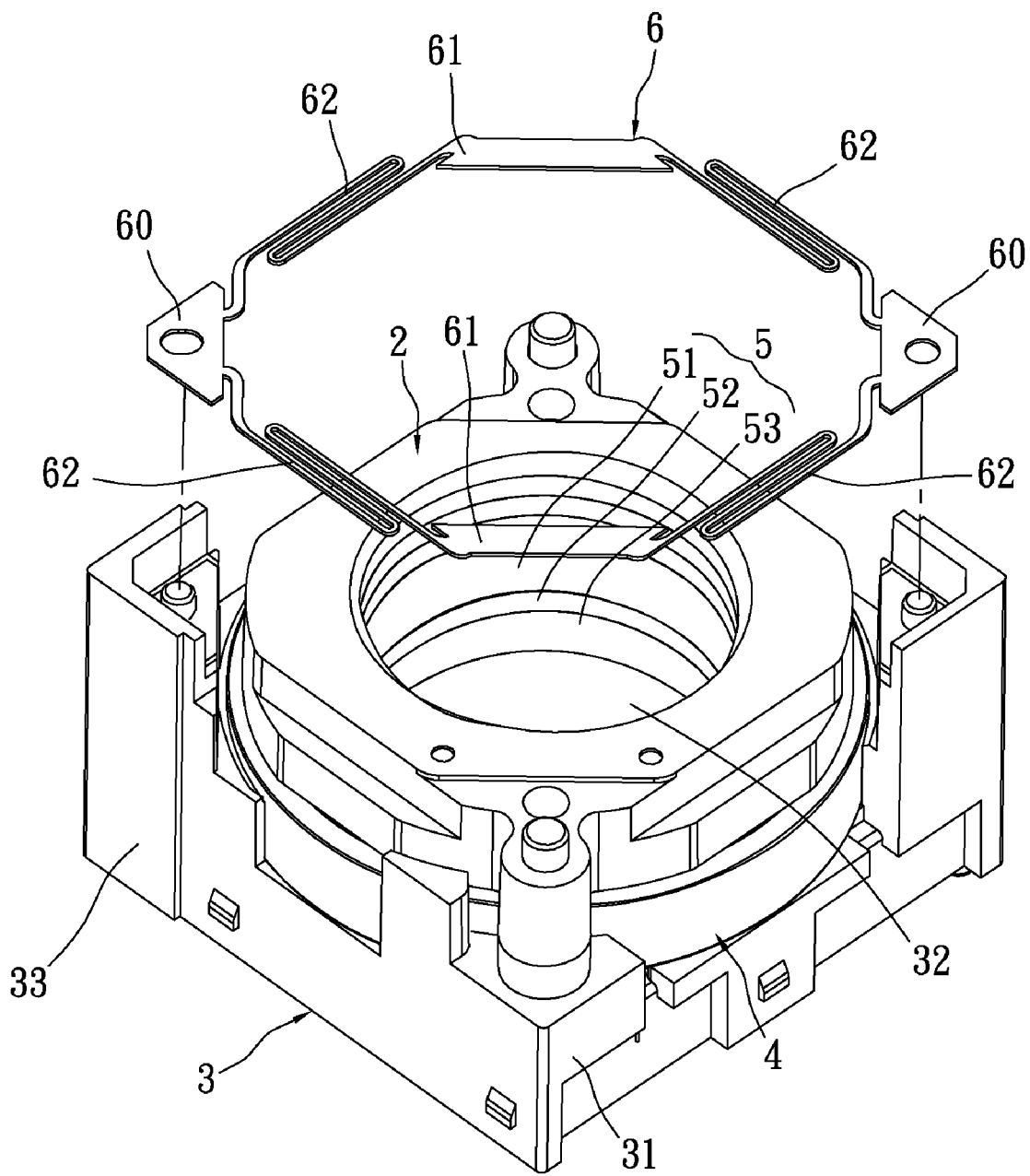
FIG. 6 is an exploded perspective view showing the lens activating device of the present invention.
Figure 7:
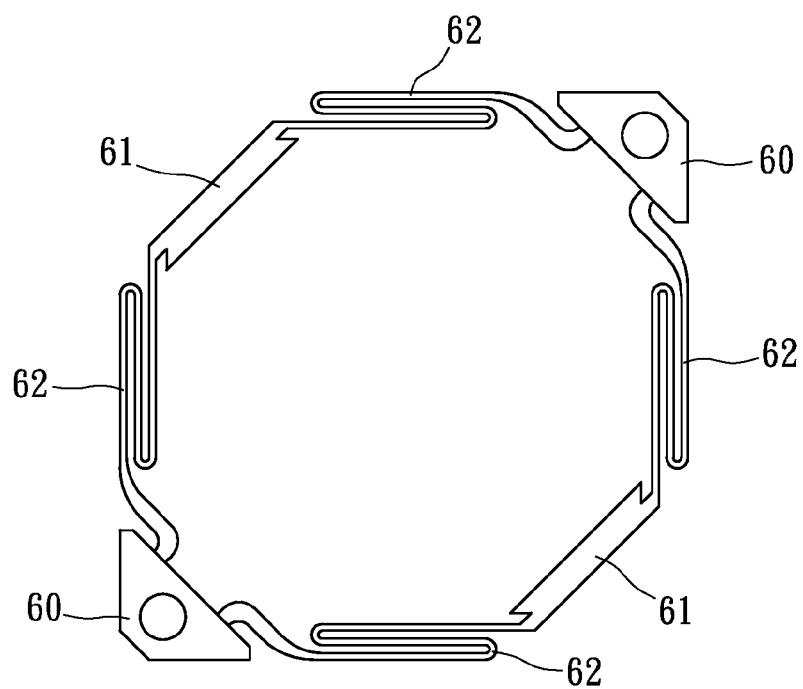
FIG. 7 is a top view showing the elastic piece of the lens activating device of the present invention.

Please refer to FIGS. 5 to 7, which show the first embodiment of the present invention. The present invention provides a lens activating device, which includes a lens assembly 2, a fixing seat 3, a coil assembly 4, at least one magnetic element 5 and at least one elastic piece 6.

The lens assembly 2 has an imaging lens (not shown). After the lens assembly 2 and the magnetic element 5 are assembled together, a movable piece of the present invention can be formed. The magnetic element 5 comprises a first magnet 51, a ferromagnetic piece 52 and a second magnet 53. The first magnet 51 and the second magnet 53 are combined to both surfaces of the ferromagnetic piece 52 with the same magnetic polarities facing to each other. Via this arrangement, the magnetic element 5 can be formed.

Furthermore, after the fixing seat 3 and the coil assembly 4 are assembled, a stationary piece of the present invention can be formed. The movable piece is connected into the stationary piece in such a manner that it is movable with respect to the stationary piece. When a current passes through the coil assembly 4, an electromagnetic field is generated. The interaction between this electromagnetic field and the magnetic lines of the magnetic element 5 generates an electromagnetic thrust, whereby the movable piece can be pushed to axially move in the stationary piece.

The above arrangement can be modified according to practical demands. The magnetic element 5 is fitted in the fixing seat 3 so as to form the stationary piece. Then, the coil assembly 4 is assembled with the lens assembly 2 so as to form the movable piece. Via the above arrangement, the same effect as the above can be achieved (this embodiment is not shown in the drawing).

In the present embodiment, the elastic piece 6 is a single loop resilient member made by means of a pressing process. The elastic piece 6 has at least two pairs of sheet portions (60, 61) and at least two pairs of elastic portions 62. The substantially symmetrically arranged sheet portions (60, 61) establish pressing contacts with the stationary and the moving pieces of the lens actuating device, and can also be referred to as the contact portions. Each set of the elastic portions 62 are serpentine and connected between every two sheet portions (60, 61) in order to make the at least one elastic piece 6 form a closed ring. Therefore, the elastic piece 6 of the present invention has a closed ring structure. As shown in the instant embodiments, the two sheet portions 60 contacting the stationary piece are disposed on the two diagonal ends of the elastic piece 6. The other two sheet portions 61 contacting the movable piece are disposed on the remaining diagonal ends of the elastic piece 6.

Further, the fixing seat 3 may have a base 31, a through-hole 32 passing through the center of the base 31, and two protrusions 33 extending from two opposite ends of the base 31. The lens assembly 2 is movably provided in the through-hole 32 of the fixing seat 3. The elastic piece 6 is assembled on the fixing seat 3 and the lens assembly 2. Two of the sheet portions 60 contact the corresponding protrusions 33 of the fixing seat 3. The other two sheet portions 61 contact the top of the lens assembly 2.

When the coil assembly 4 is supplied with electricity and interacts with the magnetic element 5, the thus-generated electromagnetic force pushes the lens assembly 2 of the movable piece to move with respect to the fixing seat 3. The lens assembly 2 also drives the other two sheet portions 61 to make them move away from the fixing seat 3 (i.e. elastic deformation). The elastic force generated by the four sets of elastic portions 62 exerts a restoring force on the lens assembly 2. Thus, when the current passing through the coil assembly 4 is adjusted or shut off, the restoring force generated by the elastic piece 6 can allow the lens assembly 2 to be positioned or restored.

Figure 8:
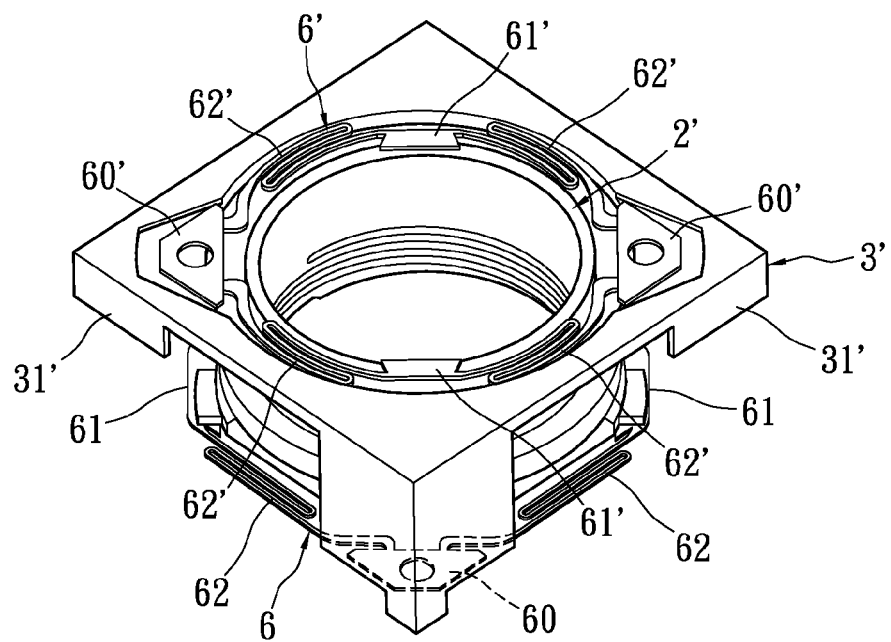
FIG. 8 is a perspective view showing the lens activating device according to another embodiment of the present invention.

Please refer to FIG. 8, which is a second embodiment of the present invention. The difference between the second embodiment and the first embodiment lies in using two elastic pieces of the present invention. The first elastic piece 6 is fixed in the same manner as that in the first embodiment. Two sheet portions 60' of the second elastic piece 6' contact the base 31'. The other two sheet portions 61' of the second elastic piece 6' contact the lens assembly 2'. Further, as the first embodiment, each set of elastic portions 62' in the second embodiment are serpentine. Each set of elastic portions 62' are connected between two sheet portions (60', 61') in order to make the at least one second elastic piece 6' form a closed ring. In addition, as for the second embodiment of the present invention, the sheet portions 60 of the first elastic piece 6 contacting the stationary piece (fixing seat 3') and the sheet portions 60' of the second elastic piece 6' contacting the stationary piece (fixing seat 3') are disposed in different diagonal ends of the fixing seat (fixing seat 3').

According to the above, by using the elastic piece (6 or 6') of a closed ring structure, the slight rotation of the movable piece in the lens activating device can be reduced. Further, the problem that the elastic piece may scrape the neighboring elements can be prevented.

The above-mentioned descriptions represent merely the preferred embodiment of the present invention, without any intention to limit the scope of the present invention thereto. Various equivalent changes, alternations or modifications based on the claims of present invention are all consequently viewed as being embraced by the scope of the present invention.

What is claimed is:

1. A lens activating device, comprising:
   at least one single-loop resilient member having at least two pairs of alternatively and substantially symmetrically arranged contact portions and elastic portions,
   wherein each pair of the contact portions is diagonally arranged on the single-loop resilient member,
   wherein each elastic portion is of serpentine structure disposed between two adjacent contact portions,
   wherein the alternatively arranged elastic and contact portions form a closed ring;
   a stationary piece in pressing contact with at least one pair of the diagonally arranged contact portions; and
   a movable piece in pressing contact with at least one remaining pair of the diagonally arranged contact portions.

2. The lens activating device according to claim 1, wherein the stationary piece includes a fixing seat, and the movable piece includes a lens assembly movably provided in the fixing seat.

3. The lens activating device according to claim 2, wherein the stationary piece further includes at least one magnetic element fitted in the fixing seat, and the movable piece further includes a coil assembly fitted in the lens assembly.

4. The lens activating device according to claim 3, wherein the magnetic element comprises a first magnet, a ferromagnetic piece, and a second magnet, wherein the first magnet and the second magnet are connected to both surfaces of the ferromagnetic piece with the same magnetic polarities facing to each other.

5. The lens activating device according to claim 2, wherein the stationary piece further includes a coil assembly fitted in the fixing seat, and the movable piece further includes at least one magnetic element fitted in the lens assembly.

6. The lens activating device according to claim 5, wherein the magnetic element comprises a first magnet, a ferromagnetic piece, and a second magnet, wherein the first magnet and the second magnet are connected to both surfaces of the ferromagnetic piece with the same magnetic polarities facing to each other.

7. The lens activating device according to claim 2, wherein the fixing seat has a base, a through-hole passing through the base, and two protrusions extending from opposite ends of the base, and the lens assembly corresponds to the through-hole.

8. The lens activating device according to claim 7, wherein the two contact portions contacting the stationary piece contact the corresponding protrusions of the fixing seat, and the other two contact portions contact the top of the lens assembly.

9. The lens activating device according to claim 7, wherein the two contact portions contacting the stationary piece contact the bottom of the base, and the other two contact portions contact the bottom of the lens assembly.

10. The lens activating device according to claim 1, wherein the two contact portions contacting the stationary piece are disposed on two diagonal ends of the single-loop resilient member, the other two contact portions contacting the movable piece are disposed on the other two diagonal ends of the single-loop resilient member.

* * * * *